United States Patent [19]

Samson et al.

[11] Patent Number: 5,462,523
[45] Date of Patent: Oct. 31, 1995

[54] DRUG DELIVERY SYSTEM

[75] Inventors: Gene Samson, Milpitas; Erik T. Engelson, Menlo Park; Hiram Chee, San Carlos; Robert E. Woodard, Fremont, all of Calif.

[73] Assignee: Target Therapeutics, Inc., Fremont, Calif.

[21] Appl. No.: 63,918

[22] Filed: May 18, 1993

[51] Int. Cl.[6] .................................................. A61M 1/00
[52] U.S. Cl. .................. 604/30; 604/246; 604/264; 604/280
[58] Field of Search ..................... 128/656, 657, 128/658, 772; 604/43, 49, 52, 53, 30, 40, 169, 170, 246, 264, 256, 267, 280

[56] References Cited

U.S. PATENT DOCUMENTS

| 399,540 | 3/1889 | Lee | 604/264 |
|---|---|---|---|
| 4,377,169 | 3/1983 | Banks | 604/8 |
| 4,708,718 | 11/1987 | Daniels | 604/53 |
| 4,717,387 | 1/1988 | Inoue et al. | 604/264 |
| 4,739,768 | 4/1988 | Engelson | 128/658 |
| 4,767,400 | 8/1988 | Miller et al. | 604/8 |
| 4,798,598 | 1/1989 | Bonello et al. | 604/280 |
| 4,953,553 | 9/1990 | Tremulis | . |
| 5,176,661 | 1/1993 | Evard et al. | 604/282 |
| 5,178,158 | 1/1993 | de Toledo | 128/772 |
| 5,195,971 | 3/1993 | Sirhan | 604/164 |
| 5,211,636 | 5/1993 | Mische | 604/264 |

Primary Examiner—C. Fred Rosenbaum
Assistant Examiner—N. Kent Gring
Attorney, Agent, or Firm—Morrison & Foerster

[57] ABSTRACT

This invention is a surgical instrument and specifically is a catheter for treating a target site by delivering a controlled amount of a therapeutic or diagnostic agent (the target site being accessible by a tortuous path through the vasculature), the perfusion tip assembly on first catheter, and a process of using that catheter to deliver fluids to the selected vascular site.

68 Claims, 4 Drawing Sheets

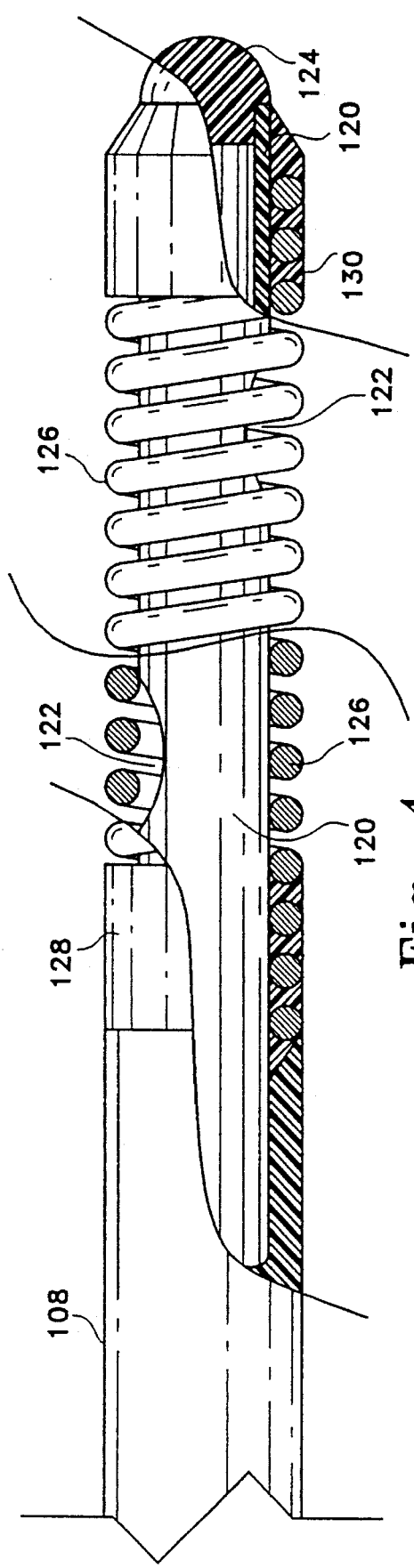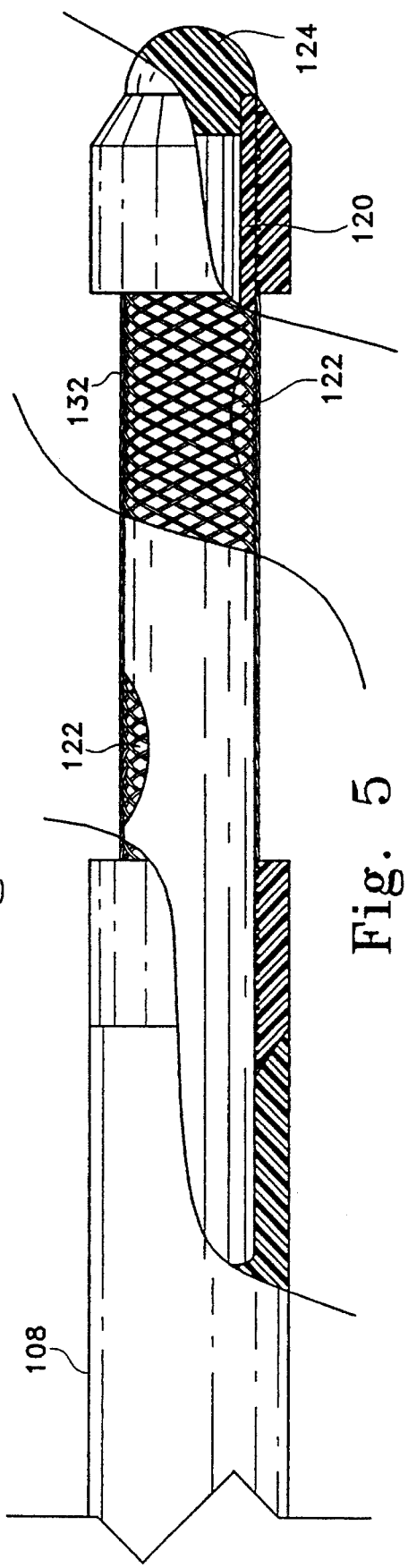

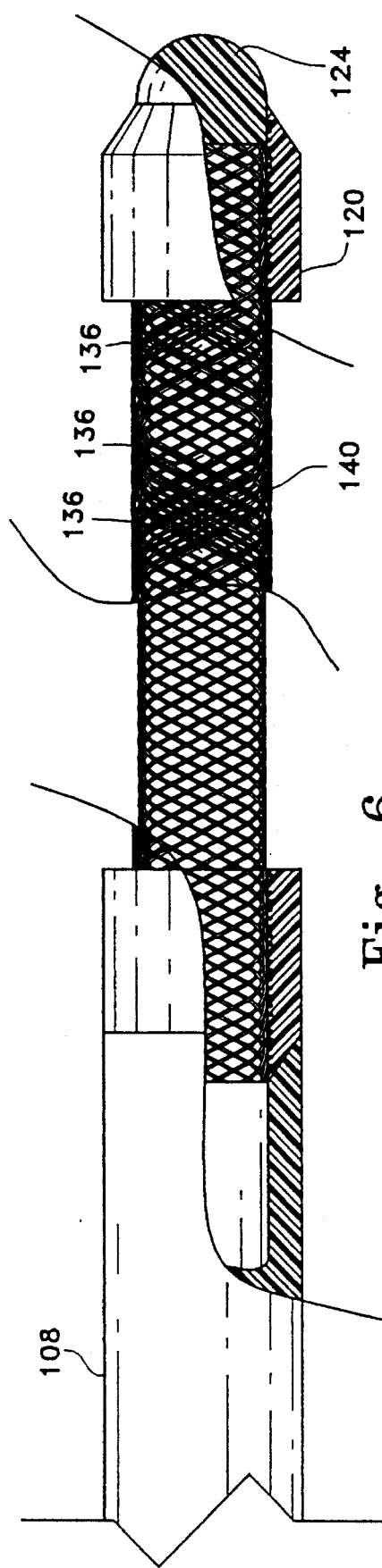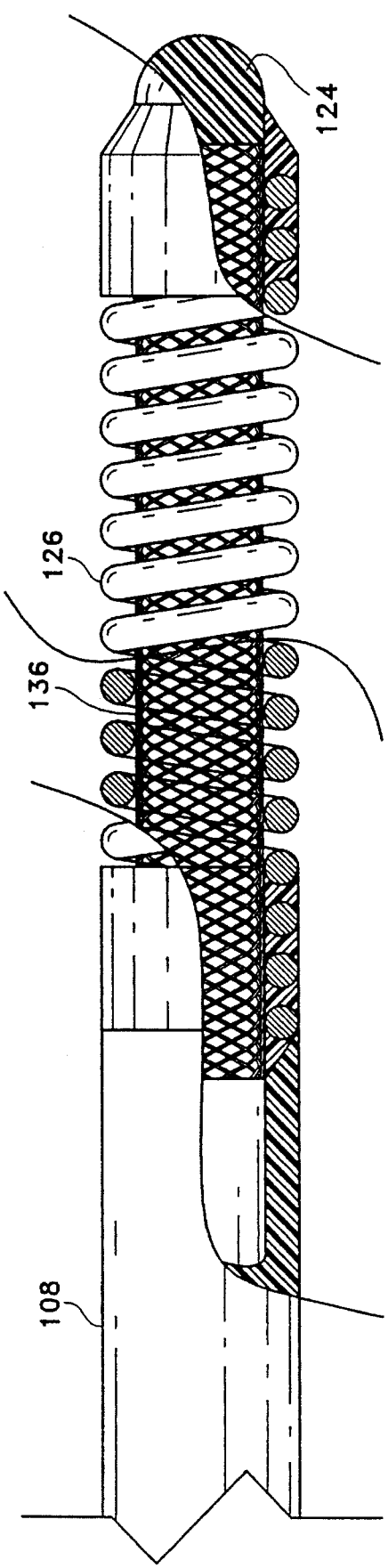

DRUG DELIVERY SYSTEM

FIELD OF THE INVENTION

This invention is a surgical instrument. Specifically, the invention includes a catheter for treating a target site within the body where the target site is accessible through a passageway in the body by delivering a controlled amount of a therapeutic or diagnostic agent. More particularly, the invention is the perfusion tip assembly on the perfusion catheter and a process of using the catheter and its perfusion tip to deliver fluids to the selected body site.

BACKGROUND OF THE INVENTION

Catheters are used as a means for delivering diagnostic or therapeutic agents to target sites within the human body that may be accessed through the circulatory system or through other systemic passageways. For example, in angiography, catheters may be used to deliver a radio-opaque agent to a target site within a blood vessel to allow radiographic viewing of the vessel and of the blood flow characteristics near the agent's release site. For the treatment of localized disease, such as a solid tumor, catheters are used to deliver a therapeutic agent to a target site within the tumor at a relatively high concentration with minimum overall side effects. Methods for producing localized vaso-occlusion in target tissue regions, by catheter injection of a vaso-occlusive agent, have also been described (U.S. Pat. No. 4,708,718 for "Hyperthermic Treatment of Tumors").

U.S. Pat. No. 4,739,768 describes a catheter having a guide wire. The catheter may be guided from an external body access site such as through the femoral artery, to an internal tissue site. The catheter progresses through a tortuous path of at least about 5 cm through vessels of less than about 3 mm inner diameter. The catheter has a relatively stiff segment dimensioned to track the wire from the access site to a region adjacent the internal tissue, and a relatively flexible remote segment dimensioned to track the wire along the tortuous path within the soft tissue. In a method for injecting a fluid into a tortuous path site, the guide wire and catheter are moved as a unit to a position adjacent the target tissue. The wire is then advanced ahead of the catheter along the tortuous path within the tissue. The catheter then tracks the wire to move along the wire's path. Once the tip of the catheter reaches the chosen site, the guide wire is removed and the selected treatment or diagnostic fluid is delivered to the target site.

Although an open catheter lumen is an effective way of delivering relatively large amounts of fluid to a selected vascular site, often it is the situation that controlled amounts of fluid must instead be delivered there. For instance, in treating certain cancerous tumors with a catheter delivering chemotherapeutic agents into the vasculature traversing the tumor, small amounts of the agent desirably would be delivered at a low rate equally over a substantial distance within the tumor.

One device for delivering controlled amounts of therapeutic or diagnostic agents to vascular sites is found in U.S. patent application No. 07/948,720, filed Sep. 27, 1992, now pending entitled "Perfusion Catheter System". This device utilizes a perfusion coil situated at the distal end of the fluid supply catheter. The fluid is introduced through the catheter lumen, through the perfusion coil, and exits through spaces found between the respective coil windings. The fluid exit rate may be actively varied by adjusting the spacing between the coil windings.

Another device suitable for delivering controllable amounts of a fluid to a selected vascular site is found in U.S. patent application No. 07/954,669, filed Sep. 30, 1992, now pending entitled "Drug Delivery Catheter With an Atraumatic Drug Delivery Tip". In this device, the fluid is delivered from the catheter lumen into the vasculature using a set of sideholes in the tip. These sideholes are of a varying size.

One variation of the inventive fluid delivery device discussed below involves the use of a regularly woven tube in which selected strands are omitted from the weave to provide fluid flow through the resulting holes created at the junction of the various strand omissions.

Other surgical or medical devices have used woven or filament containing tubes for a variety of reasons.

For instance, U.S. Pat. No. 4,767,400, to Miller et al., shows a ventricular catheter having a distal portion which is reasonably porous. The porous portion is generally formed by extruding a fiber forming polymer and winding it directly onto a mandrel. The resulting porous portion is made up of several layers of filament but cannot be characterized as being woven. The porous tip is used as a drain for removing excess cerebral spinal fluid (CSF) from a ventricle of the brain. The CSF is drained via a nonporous tubing into a vein terminating in the right atrium of the heart.

Another hydrocephalus shunt is shown in U.S. Pat. No. 4,377,169, issued Mar. 22, 1983, to Banks. This device uses a series of micro-tubes which are formed into a cylinder by mounting them about the peripheral surface of that mandrel. The tubes are then perforated using an ion beam sputter etch technique. The tubes then carry the excess CSF from the cerebral ventricles to other areas in the body.

Another porous surgical drainage tube utilizing, in this case, a metal coil is shown in U.S. Pat. No. 399,540, issued Mar. 12, 1889, to Lee et al.

The use of multi-layer materials involving filamentary layers is shown in U.S. Pat. Nos. 5,176,661, to Evard et al. and in 5,178,158 issued Jan. 12, 1993, to de Toledo. The Evard et al. reference suggests the use of wound tubular resin impregnated fibrous coverings on vascular catheters which coverings are not necessarily porous. de Toledo suggests the use of multi-filar coils having polyamide coverings thereover. Again, these tubing components are not used to exude fluid from the catheter into the body lumen except by a flow through the open end of the lumen.

Finally, several devices for allowing introduction of liquid into a body lumen or withdrawal of fluid from that body cavity are shown in U.S. Pat. No. 4,717,387, to Inoue et al., showing a Teflon frit for flushing an area with a physiological saline solution to allow visual inspection using the catheter; 4,798,598, issued Jan. 17, 1989, to Bonello et al. having a coil placed on the end of a catheter assembly through which various fluids may be introduced into the body; and 4,953,553, issued Sep. 4, 1990, to Tremulis which shows the use of perforations in a hollow guide wire suitable for monitoring pressure in a body lumen.

The present invention is a catheter assembly useful for the delivery of diagnostic or therapeutic agents to regions of the human body often accessible through systems of passageways, e.g., the vasculature and genito-urinary system. In particular, it may be used to diagnose or to treat intravascular occlusions that result from embolus or thrombus formation. The invention also includes a process for delivering fluids to those regions by use of the inventive catheter and perfusion tip.

SUMMARY OF THE INVENTION

This invention is a catheter both for use in combination with a guide wire for placement within a tortuous, small vessel and also for delivery of fluid at a select target site within the vasculature or other system of lumen within the human body. The catheter has an elongate tubular body having proximal and distal ends and a lumen extending between the ends containing the guide wire. The tubular body also has a flexible perfusion tip located at the remote or distal end for tracking the wire along the tortuous path, through small vessels to a target site and for delivery of fluid at the target site. The structure of the flexible perfusion tip also forms a portion of their invention.

A further aspect of the invention is a method for delivering a controlled amount of a therapeutic or diagnostic agent to the selected site. The method involves the placement of a catheter at a remote site in the vasculature and the delivery of the agent through that flexible inventive tip.

BRIEF DESCRIPTION OF THE DRAWINGS

FIG. 4 shows a side view (partial cutaway) of a distal fluid delivery segment in which the stiffener is polymeric tubing and the perfuser is a helical coil.

FIG. 5 shows a side view (partial cutaway) of another variation of the distal fluid delivery segment in which the stiffener is a tubing having orifices cut in its wall and the perfuser is a helical coil.

FIG. 6 shows a side view (partial cutaway) of a distal segment fluid delivery section in which the stiffener is a braided tubing and the perfuser is a similar braided tubing having certain filaments omitted to provide fluid ports.

FIG. 7 is a side view (partial cutaway) of a variation of the distal fluid delivery section in which the stiffener a braided tubing and the perfuser is a helical coil.

DESCRIPTION OF THE INVENTION

The catheter assembly of the present invention has a core or guide wire and an elongate tubular body. The elongate tubular body in the catheter assembly typically is made up of multiple segments to assure both that the catheter has sufficient stiffness to pass into the body without kinking. The distal segment often is much more flexible so that the catheter can more easily track the wire along the tortuous vessel pathway. The distal flexible segment also includes at least one flexible perfusion section which allows a controllable flow of fluid to a selected target site within the chosen vessel. The inventive perfusion tip is made of a material that is biologically compatible and, optionally, may be visible when exposed to x-ray. The perfusion tip is constructed in such a way that fluids introduced into the catheter at the proximal end perfuse out of openings in the tip. The tip is made up of two major components: an inner stiffener portion which is relatively porous and an outer perfuser layer which desirably controls fluid flow to a relatively lower rate. The tip inner stiffener may be in the form of a coil wound from wire or ribbon, a braid, or other appropriate configurations such as perforated micropiping. The perfuser layer may be a coil, a braid, but most preferably is a braided tube in which selected filaments have been removed.

The following representative embodiments are illustrative only and in no way limit the invention.

Figure 1:
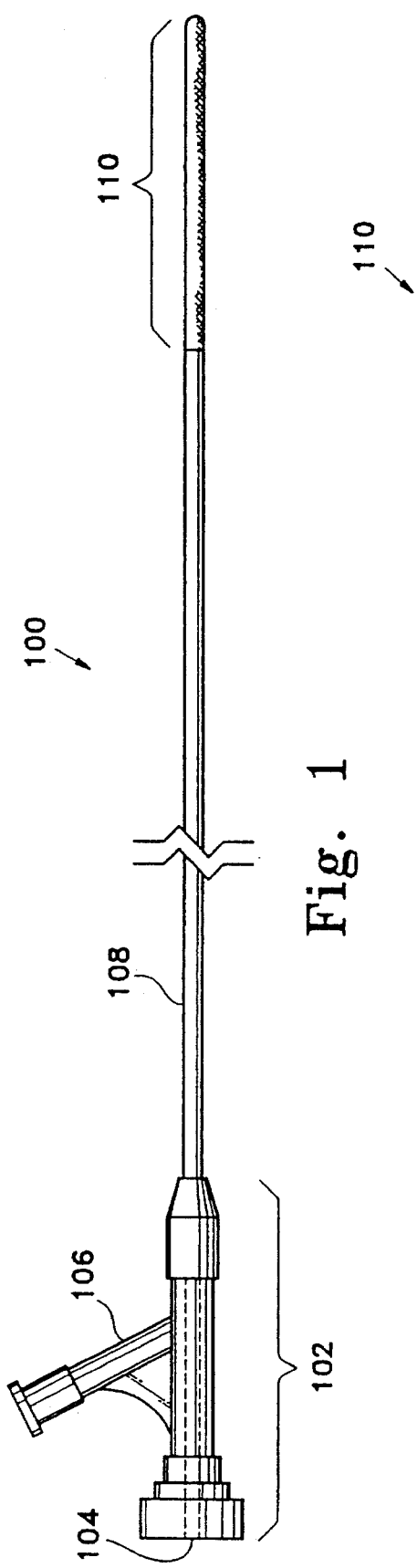
FIG. 1 shows a catheter with a coil tip constructed according to one embodiment of the present invention.

FIG. 1 shows one embodiment of a catheter assembly made according to the invention. The catheter assembly, generally designated (100), includes a catheter housing and a guidewire which is not shown. The assembly may include a standard proximal end fitting (102) having a side or infusion port (106) and a guidewire port (104). Through the axial center of the proximal end fitting (102) may be found a guidewire port (104) through which the guidewire is received. Attached to the proximal end fitting is a catheter body (108) which axially lines up with the guidewire port (104) in the proximal end fitting (102). The catheter body is a tubular body that extends distally to the perfusion tip (110) which is discussed in more detail below. The catheter body may be of a variety of suitable shapes and lengths, depending upon the service to which it is placed, but generally it is desired that a two or three segment catheter body construction be used. Such a catheter construction is shown in U.S. Pat. 4,739,768, to Engelson. This construction provides that the most proximate portion of the catheter body is the most stiff and the middle portion, if a middle portion having sufficient characteristics is selected, is somewhat more flexible. The most distal portion near the perfusion tip (110) is the most flexible. In this way, the catheter assembly may be maneuvered using a guidewire into very tight portions of the body's vasculature. The Engelson patent provides details on the manner of construction of such a catheter body and its use in traversing the human body.

Figure 2:
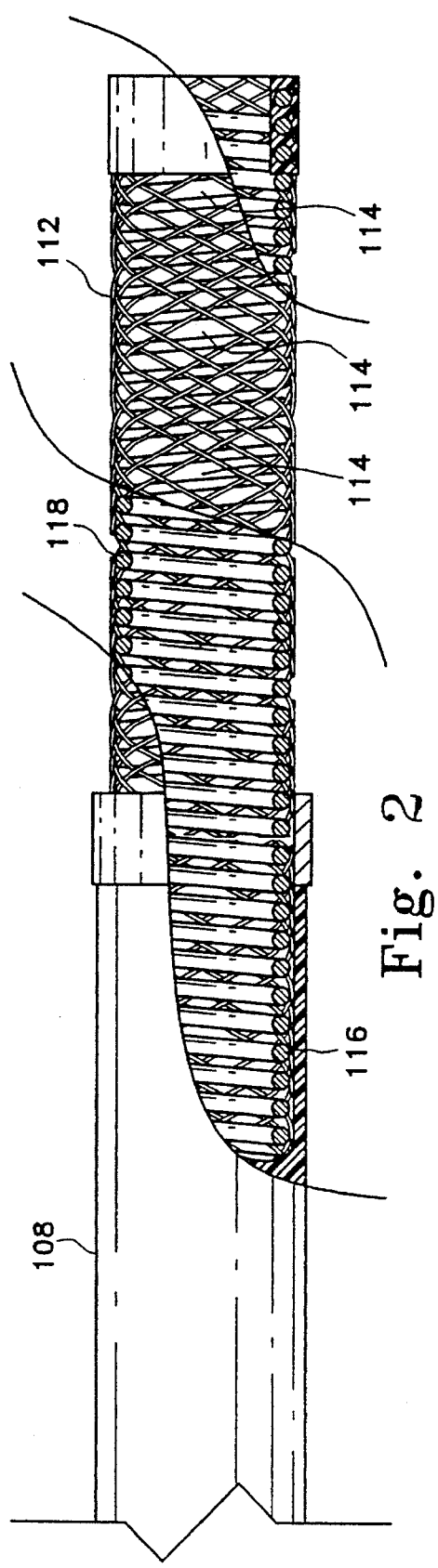
FIG. 2 shows a side view (partial cutaway) of the inventive distal fluid delivery segment in which the stiffener is a coil and the perfuser is woven tubing having spaced omission orifices within the wall of that tubing.

The most distal section found in FIG. 1 is a very desirable variation of the perfusion tip made according to this invention. This perfusion tip is shown in FIG. 2 in greater detail and is made of a filamentary outer braid or perfuser (112) from which certain filaments have been removed from the regularly spaced braid to provide what we term "regularly spaced omission orifices" (114) which definition is discussed below. Supporting the dacron filament braid (112) within the closed portion of the catheter body is a secondary coil (116). The secondary coil (116) merely serves to provide support for the inside of the tubing used as the catheter body (108). The spaced omission orifices (114) and their surrounding braided area are supported by a main coil (118). Main coil (118) has the function of supporting the braid and allowing fluid within to pass to the braid and thence out into the space beyond the braid. The inner stiffener for this variation and the others discussed below each allow a significant higher liquid flow rate than the surrounding perfuser covering it for a particular pressure differential. Said another way, imposition of a specific pressure on the interior of the inner stiffener (without the center perfuser in place) will result in a significantly higher liquid flow rate (or "index flow rate") than will the exterior perfuser layer upon imposition of the same interior pressure. The most distal end of the perfuser tip may be closed with a cap or other suitable device for closing the end of the coil. Where appropriate, however, the distal end of the perfuser tip may be left open to accommodate a guidewire. In such instances, the braid or perfuser (112) may extend past the distal end of the main coil (118). A braided perfuser will taper to near closure within three to four diameters past the distal end of the main coil (118). These various junctions may be glued together or otherwise suitably attached to each other. Desirably the main coil (118) is screwed into the secondary coil (116).

Figure 3:
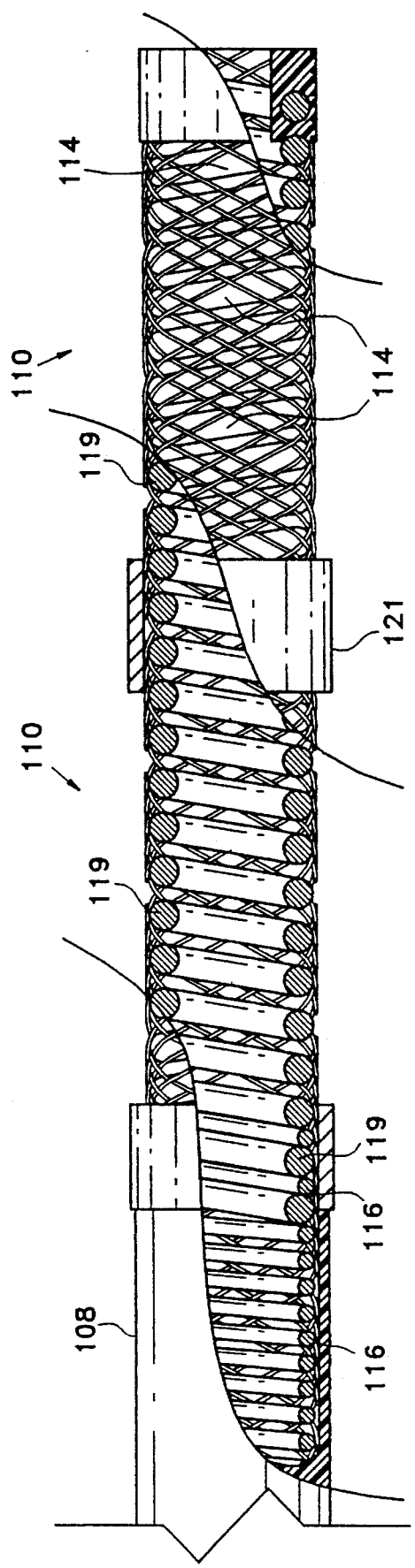
FIG. 3 shows a side view (partial cutaway) of a variation of the perfusion tip shown in FIG. 2 having multiple sections of porosity.

FIG. 3 shows a further variation having multiple perfuser sections (119) separated by a less porous section (121). The less porous section may be nonporous to the passage of fluid. Such a variation may be used to simultaneously treat multiple lesions or various thromboli within a single vessel. The less porous section (121) may be a secondary coil as is shown in FIG. 2 or may be a short section of polymeric tubing or other similar inserts placed within or without the perfusion section. Alternatively, a small portion of the braid may be treated to make it nonporous.

The braiding used in this invention is relatively straightforward to produce. Commercial machinery suitable for making braids of this small diameter are available. These desirably are made from dacron, silk, or other suitable biocompatible materials. One appropriate way of producing the woven tubing is one in which sixteen strands are interwoven or "regularly woven" to produce a sock-like construction. That is to say that, viewed from the axis or end of the tubing, as a filament passes around the circumference of the tubing, it alternates position—in and out—with filaments passing around the circumference in the other direction. One strand of the eight woven in each direction may be omitted to produce a desirable perfuser layer. The site where the pathways resulting from the missing strands cross are the so-called "omission orifices". Of course, it should be apparent that any number of filaments may be woven into the tubing so long as the ultimate size and porosity of the final product is in keeping with its use as a perfusion device.

FIG. 4 shows another variation of the inventive perfuser tip which may be used as (110) in FIG. 1.

In this variation, the stiffener (120) is a polyimide tube or other similar tube having a number of orifices or slits (122) therein. A cap or closure (124) may be placed at the distal end of the perfuser tip. However, as was the case above, it is desirable to leave the end of the perfuser tip open to provide room for a guidewire and guide tip. Again, it is preferred that the perfuser extend for several diameters past the end of the inner stiffener. Placed on the outside of the stiffener (120) is a perfuser coil (126) which is wound in such a fashion as to control and equalize flow from the interior of the perfuser tip through slits (122) and out through coil (126). This control is had by choice of the size of the wire utilized in coil (126), the pitch of those windings, and the resultant spacing between adjacent coil windings. Again, the pitch of the coil may be maintained and the inner perfuser (120) and the cap (124) all held in place by epoxy or other suitable adhesive joints at (128) and (130).

FIG. 5 is a further variation of the perfuser tip as might be found at (110) in FIG. 1. Again, in this structure, (108) is the wall of the catheter leading to this perfuser tip. As was the structure with FIG. 5, the inner stiffener (120) is of a suitable material, typically a polyimide, and contains slits (122), as did the device shown in FIG. 4. Instead of the coils utilized as the fluid perfuser layer seen in FIG. 3, this variation utilizes a braid (132), regularly wound, with or without the regularly spaced omission orifices.

FIG. 6 depicts a variation of the invention in which the inner stiffener is a braided tube of a reasonably stiff filament. The filament may be made stiff by using a larger denier filament or by appropriate selection of the polymer making up the braided tube support layer (136). The stiffener braid may also be metallic and woven from metallic wires such as platinum, stainless steel, and other suitable biocompatible metals. The outer or perfuser covering (140) may be made in the same fashion as that shown in FIG. 2. Desirably the outer perfuser covering utilizes the regularly spaced omission orifices. The end of the perfuser tip may be capped at (124) or fused or otherwise closed in some known fashion but preferably is not closed to allow for guidewire use.

FIG. 7 shows another variation in which the inner stiffener (136) is made in the same fashion as the stiffener found in FIG. 6. In this instance, the perfuser is a perfuser coil (126) similar in construction to that shown in FIG. 4.

The perfuser tip shown in each of the Figures typically has an outer diameter of about 0.005 to 0.065 inches but preferably is about 0.020 to 0.045 inches. The axial length of the tip will be normally between about 2 and 300 mm but preferably is between 5 and 100 mm in length. The coils used in these tips are preferably of metal or an alloy such as stainless steel, platinum, platinum alloys (particularly platinum and tungsten), inconel, or other biologically compatible metals. The wires used in the coils typically have a diameter between 0.001 and 0.010 inches. Although the coils may be wound in such a way that the pitch is constant when used as a perfuser layer, it is also within the scope of this invention that the coils are wound with a variable pitch so as to provide areas of higher fluid flow. Similarly, when a coil is used as the stiffener layer, the coil may be wound in such a way as to be either of a constant pitch or a variable pitch. A constant pitch coil having openings between adjacent wires is often desirable from the point of ease of fluid flow. However, variable pitched coils may be useful in those instances where the fluid to be provided to the vasculature is slightly viscous or additional spacing is required to allow ease of fluid flow from the inside of the catheter.

In operation, this fluid delivery device is used in much the same way as are others found in this service. For instance, a guidewire is inserted into the lumen of the catheter body, such as that shown in FIG. 1. The guidewire will extend into the catheter body until it passes through the distal and at the perfusion tip where the tip is open or it abuts the most distal portion of perfusion tip (110) where the tip is closed. The assembly is then guided through the vasculature to the target site. The catheter body is guided over the guidewire to the target site. The guidewire may, if the situation demands, be removed. Fluid is then injected through the various proximal end fittings (106) and into the catheter lumen. The fluid perfuses out through the inner stiffener at the outer perfusion layer and into the target site at the desired rate. The fluid may be a radiopaque agent, chemotherapeutic agent, a clot-dissolving agent, a vasoocclusive agent, or any fluid which is desirably delivered to that site.

Modification of the above-described methods for carrying out the invention, and variations of the mechanical aspects of the invention that are obvious to those of skill in the mechanical and guidewire and/or catheter arts are intended to be within the scope of the following claims.

I claim as my invention:

1. A fluid delivery tip for delivery of fluid through a catheter, said tip having a proximal end adapted to connect to a catheter body, a distal end, and an axis extending between said proximal and distal ends, comprising a stiffener and a perfuser:

said stiffener extending axially between the proximal tip end and the distal tip end, having an inner stiffener surface and an outer stiffener surface, which stiffener is stiffer than the perfuser, and having openings to allow fluid flow from the inner stiffener surface to the outer stiffener surface at a high index flow rate, and said perfuser having an inner perfuser surface, an outer perfuser surface, located at and which is in contact with the outer stiffener surface, coaxial to the stiffener and extending axially between the proximal tip end and the distal tip end and adapted to allow fluid flow from the outer stiffener surface to the outer perfuser surface at an index fluid flow rate relatively lower than the stiffener index flow rate.

2. The fluid delivery tip of claim 1 where the stiffener comprises a helical coil.

3. The fluid delivery tip of claim 2 where the perfuser comprises a regularly woven filamentary tube having regularly spaced omission orifices within the wall of said tube.

4. The fluid delivery tip of claim 2 where the perfuser comprises a helical coil.

5. The fluid delivery tip of claim 4 where the helical coil perfuser has regular windings.

6. The fluid delivery tip of claim 4 where the helical coil perfuser has intermittent regular windings.

7. The fluid delivery tip of claim 1 where the stiffener comprises tubing with a wall having orifices in the tubing wall.

8. The fluid delivery tip of claim 7 where the perfuser comprises a regularly woven filamentary tube having regularly spaced omission orifices within the wall of said tube.

9. The fluid delivery tip of claim 7 where the perfuser comprises a helical coil.

10. The fluid delivery tip of claim 9 where the helical coil perfuser has regular windings.

11. The fluid delivery tip of claim 9 where the helical coil perfuser has intermittent regular windings.

12. The fluid delivery tip of claim 1 where the stiffener comprises a tubing of woven filament.

13. The fluid delivery tip of claim 12 where the perfuser comprises a regularly woven filamentary tube having regularly spaced omission orifices within the wall of said tube.

14. The fluid delivery tip of claim 12 where the perfuser comprises a helical coil.

15. The fluid delivery tip of claim 14 where the helical coil perfuser has regular windings.

16. The fluid delivery tip of claim 14 where the helical coil perfuser has intermittent regular windings.

17. The fluid delivery tip of claim 1 where the perfuser comprises a regularly woven filamentary tube having regularly spaced omission orifices within the wall of said tube.

18. The fluid delivery tip of claim 1 where the perfuser comprises a helical coil.

19. The fluid delivery tip of claim 18 where the helical coil perfuser has regular windings.

20. The fluid delivery tip of claim 18 where the helical coil perfuser has intermittent regular windings.

21. The fluid delivery tip of claim 1 additionally comprising radiopaque markers at the distal tip end and at the proximal tip end.

22. The fluid delivery tip of claim 1 additionally comprising a closure at the distal tip end to substantially prevent axial fluid flow from the distal tip end.

23. The fluid delivery tip of claim 1 comprising multiple stiffeners and perfusers spaced apart along the axis of the tip in the region of the distal tip end and separated by regions of lower porosity.

24. A catheter assembly comprising:

a catheter body of an elongate tube with a proximate and a distal end with an open lumen extending between the proximate and distal catheter body, and a fluid delivery tip for delivery of fluid supplied through the catheter body lumen, said tip having a proximal and a distal tip end having a stiffener and perfuser, said stiffener extending axially between the proximal tip end and the distal tip end, having an inner stiffener surface and an outer stiffener surface, which stiffener is stiffer than said perfuser, and having openings to allow fluid flow from the inner stiffener surface to the outer stiffener surface at a high index flow rate, and said perfuser having an inner perfuser surface, an outer perfuser surface, which perfuser is located at the outer stiffener surface, coaxial to and which is in contact with the stiffener and extending axially between the proximal tip end and the distal tip end and adapted to allow fluid flow from the outer stiffener surface to the outer perfuser surface at an index fluid flow rate relatively lower than the stiffener index flow rate.

25. The catheter assembly of claim 24 where the stiffener comprises a helical coil.

26. The catheter assembly of claim 25 where the perfuser comprises a helical coil.

27. The catheter assembly of claim 26 where the helical coil perfuser has regular windings.

28. The catheter assembly of claim 26 where the helical coil perfuser has intermittent regular windings.

29. The catheter assembly of claim 25 where the perfuser comprises a regularly woven filamentary tube having regularly spaced omission orifices within the wall of said tube.

30. The catheter assembly of claim 24 where the stiffener comprises tubing with a wall having orifices in the tubing wall.

31. The catheter assembly of claim 30 where the perfuser comprises a regularly woven filamentary tube having regularly spaced omission orifices within the wall of said tube.

32. The catheter assembly of claim 30 where the perfuser comprises a helical coil.

33. The catheter assembly of claim 32 where the helical coil perfuser has regular windings.

34. The catheter assembly of claim 24 where the stiffener comprises a tubing of woven filament.

35. The catheter assembly of claim 34 where the perfuser comprises a helical coil.

36. The catheter assembly of claim 35 where the helical coil perfuser has regular windings.

37. The catheter assembly of claim 35 where the helical coil perfuser has intermittent regular windings.

38. The catheter assembly of claim 32 where the helical coil perfuser has intermittent regular windings.

39. The catheter assembly of claim 34 where the perfuser comprises a regularly woven filamentary tube having regularly spaced omission orifices within the wall of said tube.

40. The catheter assembly of claim 24 where the perfuser comprises a regularly woven filamentary tube having regularly spaced omission orifices within the wall of said tube.

41. The catheter assembly of claim 24 where the perfuser comprises a helical coil.

42. The catheter assembly of claim 41 where the helical coil perfuser has regular windings.

43. The catheter assembly of claim 41 where the helical coil perfuser has intermittent regular windings.

44. The catheter assembly of claim 24 additionally comprising radiopaque markers at the distal tip end and at the proximal tip end.

45. The catheter assembly of claim 24 additionally comprising a closure at the distal tip end to substantially prevent axial fluid flow from the distal tip end.

46. The fluid delivery tip of claim 24 comprising multiple stiffeners and perfusers spaced apart along the axis of the tip in the region of the distal tip end and separated by regions of lower porosity.

47. A fluid delivery tip for delivery of fluid through a catheter, said tip having a proximal end adapted to connect to a catheter body, a distal end, and an axis extending between said proximal and distal ends, comprising a stiffener and a perfuser:

said stiffener extending axially between the proximal tip end and the distal tip end, having an inner stiffener surface and an outer stiffener surface, which stiffener is stiffer than said perfuser, and having openings to allow fluid flow from the inner stiffener surface to the outer stiffener surface, and said perfuser comprising a woven filamentary tube having an inner perfuser surface, an outer perfuser surface, located at the outer stiffener surface, coaxial to the stiffener and extending axially between the proximal tip end and the distal tip end and adapted to allow fluid flow from the outer stiffener surface to the outer perfuser surface.

48. The fluid delivery tip of claim 47 where the stiffener comprises a helically wound coil.

49. The fluid delivery tip of claim 48 where the perfuser has regularly spaced omission orifices within the wall of said tube.

50. The fluid delivery tip of claim 47 where the stiffener comprises tubing with a wall having orifices in the tubing wall.

51. The fluid delivery tip of claim 50 where the perfuser has regularly spaced omission orifices within the wall of said tube.

52. The fluid delivery tip of claim 47 where the stiffener comprises a woven filamentary tube.

53. The fluid delivery tip of claim 52 where the perfuser comprises a regularly woven filamentary tube having regularly spaced omission orifices within the wall of said tube.

54. The fluid delivery tip of claim 47 where the perfuser has regularly spaced omission orifices within the wall of said tube.

55. The fluid delivery tip of claim 47 additionally comprising radiopaque markers at the distal tip end and at the proximal tip end.

56. The fluid delivery tip of claim 47 additionally comprising a closure at the distal tip end to substantially prevent axial fluid flow from the distal tip end.

57. The fluid delivery tip of claim 47 comprising multiple stiffeners and perfusers spaced apart along the axis of the tip in the region of the distal tip end and separated by regions of lower porosity.

58. A catheter assembly comprising:

a catheter body of an elongate tube with a proximate and a distal end with an open lumen extending between the proximate and distal catheter body, and a fluid delivery tip for delivery of fluid supplied through the catheter body lumen, said tip having a proximal and a distal tip end having a stiffener and a perfuser, said stiffener extending axially between the proximal tip end and the distal tip end, having an inner stiffener surface and an outer stiffener surface, which stiffener is stiffer than said perfuser, and having openings to allow fluid flow from the inner stiffener surface to the outer stiffener surface, and said perfuser comprising a woven filamentary tube having an inner perfuser surface, an outer perfuser surface, located at the outer stiffener surface, coaxial to the stiffener and extending axially between the proximal tip end and the distal tip end and adapted to allow fluid flow from the outer stiffener surface to the outer perfuser surface.

59. The catheter assembly of claim 58 where the stiffener comprises a helical coil.

60. The catheter assembly of claim 59 where the perfuser has regularly spaced omission orifices within the wall of said tube.

61. The catheter assembly of claim 58 where the stiffener comprises tubing with a wall having orifices in the tubing wall.

62. The catheter assembly of claim 61 where the perfuser has regularly spaced omission orifices within the wall of said tube.

63. The catheter assembly of claim 58 where the stiffener comprises a tubing of woven filament.

64. The catheter assembly of claim 63 where the perfuser has regularly spaced omission orifices within the wall of said tube.

65. The catheter assembly of claim 58 where the perfuser has regularly spaced omission orifices within the wall of said tube.

66. The catheter assembly of claim 58 additionally comprising radiopaque markers at the distal tip end and at the proximal tip end.

67. The catheter assembly of claim 58 additionally comprising a closure at the distal tip end to substantially prevent axial fluid flow from the distal tip end.

68. The catheter assembly of claim 58 comprising multiple stiffeners and perfusers spaced apart along the axis of the tip in the region of the distal tip end and separated by regions of lower porosity.

* * * * *